US009005525B2

(12) United States Patent
Noyes et al.

(10) Patent No.: US 9,005,525 B2
(45) Date of Patent: Apr. 14, 2015

(54) TRANSPORTABLE, SELF-CONTAINED ASSAY FACILITY AND METHOD OF USING SAME TO PROCURE AND ASSAY PRECIOUS METALS

(71) Applicants: Chris M. Noyes, Suffolk, VA (US); Walter Nadonza, Virginia Beach, VA (US)

(72) Inventors: Chris M. Noyes, Suffolk, VA (US); Walter Nadonza, Virginia Beach, VA (US)

(73) Assignee: AOW Holdings, LLC, Chesapeake, VA (US)

( * ) Notice: Subject to any disclaimer, the term of this patent is extended or adjusted under 35 U.S.C. 154(b) by 292 days.

(21) Appl. No.: 13/731,163

(22) Filed: Dec. 31, 2012

(65) Prior Publication Data

US 2013/0118948 A1    May 16, 2013
US 2014/0353205 A9    Dec. 4, 2014

Related U.S. Application Data

(63) Continuation-in-part of application No. 13/364,422, filed on Feb. 2, 2012, now Pat. No. 8,551,402, which is a continuation-in-part of application No. 13/136,811, filed on Aug. 11, 2011, now abandoned, said (Continued)

(51) Int. Cl.
| | |
|---|---|
| *G01N 21/00* | (2006.01) |
| *C22B 11/00* | (2006.01) |
| *B60P 3/14* | (2006.01) |
| *G01N 23/223* | (2006.01) |
| *G01N 33/20* | (2006.01) |

(52) U.S. Cl.
CPC . *C22B 11/00* (2013.01); *B60P 3/14* (2013.01); *G01N 23/223* (2013.01); *G01N 33/20* (2013.01); *G01N 2223/301* (2013.01); *G01N 2223/076* (2013.01)

(58) Field of Classification Search
USPC .............. 422/63–66, 502–503; 436/180; 296/24.3
See application file for complete search history.

(56) References Cited

U.S. PATENT DOCUMENTS

| | | |
|---|---|---|
| 1,444,025 A | 2/1923 | Copp |
| 1,557,431 A | 10/1925 | Davignon |
| 1,764,057 A | 6/1930 | Steinhauer |

(Continued)

FOREIGN PATENT DOCUMENTS

| | | |
|---|---|---|
| KR | 10-2007-0072373 | 7/2007 |
| WO | WO 2013022473 A1 | 2/2013 |

OTHER PUBLICATIONS

Feb. 14, 2013, International Search Report PCT/US2011/066807.

(Continued)

*Primary Examiner* — Jyoti Nagpaul
(74) *Attorney, Agent, or Firm* — Neifeld IP Law, PC

(57) ABSTRACT

A transportable, self-contained assay facility built in a modified standard shipping container that is completely equipped to melt and assay precious metals, particularly gold and silver. An induction furnace melts the metal that is then poured into an ingot. The ingot is weighed and analyzed using an XRF alloy analyzer and the percentage of gold and/or other metals recorded. The value of the gold at current market prices is calculated and the assay and the value of the ingot is printed and given to the seller. The seller may opt to receive the ingot and pay the assayer an assay fee. Alternately, the seller may ask to be paid in cash, by bullion, wire transfer, or by an open hedge. A transfer or hedge is initiated and confirmed from the assay facility. The ingots may be securely stored in a safe within the assay facility.

19 Claims, 12 Drawing Sheets

Related U.S. Application Data application No. 13/731,163 is a continuation-in-part of application No. PCT/US2011/066807, filed on Dec. 22, 2011, which is a continuation-in-part of application No. 13/136,811, filed on Aug. 11, 2011, now abandoned.

(56) References Cited

U.S. PATENT DOCUMENTS

| | | | |
|---|---|---|---|
| 3,497,093 | A | 2/1970 | Mardiat, Sr. |
| 3,697,123 | A | 10/1972 | Gygrynuk |
| 4,462,879 | A | 7/1984 | Castellanos et al. |
| 4,643,476 | A | 2/1987 | Montgerard |
| 6,688,048 | B2 | 2/2004 | Staschik |
| 7,290,817 | B1 | 11/2007 | Delasse |
| 8,329,105 | B1 | 12/2012 | Sweeny et al. |
| 8,551,402 | B1 | 10/2013 | Noyes |
| 2005/0234602 | A1 | 10/2005 | Rigsby |
| 2005/0247162 | A1 | 11/2005 | Bratina |
| 2008/0115600 | A1 | 5/2008 | Hageluken et al. |
| 2010/0305957 | A1 | 12/2010 | Parsons et al. |
| 2011/0047062 | A1 | 2/2011 | Kerschner et al. |
| 2012/0030097 | A1 | 2/2012 | Hagan et al. |
| 2013/0118948 | A1 | 5/2013 | Noyes |

OTHER PUBLICATIONS

Written Opinion PCT/US2011/066807, mailed Sep. 19, 2012.
Northern Refineries, "Northern Refineries—Refining Process of Precious Metals" http://web.archive.org/web/20060512215825/http://www.northernrefineries.com/Refining_Process.htm (May 12, 2006).
Feb. 17, 2010, San Diego Refining Co., "San Diego Refining" http://web.archive.org/web/20100217040549/http://sandiegorefining.com/assaying.html.
Gold Refining Forum.com, http://goldrefiningforum.com/~goldrefi/phpBB3/viewtopic.php?f=60&t=10402&start=0, (Aug. 13, 2013).
Office Action mailed Sep. 6, 2013 in related U.S. Appl. No. 13/136,803.
Petition to Accept Unintentionally Delayed Priority Claim filed Nov. 25, 2013 in related U.S. Appl. No. 13/364,422.
Nov. 22, 2013, Petition to Accept Unintentionally Delayed Priority Claim filed Nov. 22, 2013 in related U.S. Appl. No. 13/731,163.
Petition to Accept Unintentionally Delayed Priority Claim filed Nov. 25, 2013 in related U.S. Appl. No. 13/863,622.
Nov. 22, 2013 Declaration of Chris Noyes submitted in O-008-O-010.
Declaration of Amanda Story submitted in O-008-O-010.
PCT International Search Report, PCT/IB2013/061345.
PCT Written Opinion, PCT/IB2013/061345.
PCT International Search Report, PCT/IB2013/061454.
PCT Written Opinion, PCT/IB2013/061454.
Feb. 17, 2010, San Diego Refining Co., "San Diego Refining" http://web.archive. org/web/20100217040549/http://sandiegorefining.com/assaying.html.
Petition to Accept Unintentionally Delayed Priority Claim filed Nov. 22, 2013 in related U.S. Appl. No. 13/731,163.
Petition to Accept Unintentionally Delayed Priority Claim filed Nov. 25, 2013 in U.S. Appl. No. 13/863,622.
Nov. 22, 2013, Declaration of Chris Noyes submitted in O-008-O-010.
PCT International Search Report, PCT/IB203/061345.
PCT Written Opinion, PCT/IB203/061345.

2040 Precious Metals

Time 4.6 sec
RedAu 14K   1.7

| Ele | % | +/−2σ |
|-----|-------|--------|
| Au  | 59.66 | 0.88   |
| Ag  | 6.54  | 0.38   |
| Pd  | nd    | <0.057 |
| Pt  | nd    | <1.21  |
| Zn  | 8.99  | 0.44   |
| Cu  | 24.81 | 0.69   |

[Main]

Fig. 7 www.assayonwheels.com

Truck 001 CHRIS Data

Speed, Convenience and Transparency

390

Date: 11/2/2012
Customer: Select One
Processor: Select One

Gold Assay
Gold Bar 1

| | | |
|---|---|---|
| X-ray 1 | 0.0000 | |
| X-ray 2 | 0.0000 | |
| X-ray 3 | 0.0000 | |
| X-ray 4 | 0.0000 | |
| X-ray 5 | 0.0000 | Formula: |
| 392 — % of Pure | 0.00% | (Average of x-ray spots in percent) |
| 394 — Bar Karat | 0.0 | (Average*24) |
| 396 — Gram Bar Weight | | (Weight of Bar in Grams) |
| 398 — Total Ounces of Pure | 0.000 | (% of Pure*Weight/31.1) |
| 400 — Market Price | | (Current Gold Market Price) |
| 402 — Total Amount | $0.00 | (Total Ounces*Market Price) |
| 404 — Payout Percentage | Select One | |
| 406 — Payout Total | $0.00 | (Total Amount * Percentage) |
| 408 — Processing Fee | Select One | (Set fee) |
| — Shipping Cost | $0.00 | (Total Ounces*$4) |

410 — Customer Payout    $0.00    (Payout Total-Processing-Shipping)

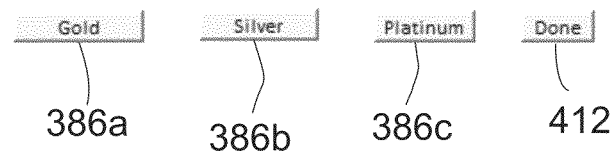

386a    386b    386c    412

Fig. 8b

TRANSPORTABLE, SELF-CONTAINED ASSAY FACILITY AND METHOD OF USING SAME TO PROCURE AND ASSAY PRECIOUS METALS

CROSS REFERENCE TO RELATED APPLICATIONS

This application Ser. No. 13/731,163, filed Dec. 31, 2012 is a Continuation-in-Part of application Ser. No. 13/364,422, filed Feb. 2, 2012, issued as U.S. Pat. No. 8,551,402, Oct. 8, 2013, which is a Continuation-in-Part of application Ser. No. 13/136,811, filed Aug. 11, 2011, both of which are incorporated by reference herein in their entirety; and Application Ser. No. 13/731,163, filed Dec. 31, 2012 is a Continuation-in-Part of Application No. PCT/US2011/066807, filed Dec. 22, 2011, which is a Continuation-in-Part of application Ser. No. 13/136,811, filed Aug. 11, 2011.

FIELD OF THE INVENTION

The invention pertains to facilities for assaying precious metals and, more particularly, to a secure, transportable, self-contained assay facility packaged in a standardized shipping container and a method of using the facility to procure, assay, and process gold and other precious metals.

BACKGROUND OF THE INVENTION

The increasing demand for gold and other precious metals for industrial processes, investments, and other uses has caused the market prices for such metals to increase to record levels. The high market price of gold has prompted owners of gold and other precious metals to frequent establishments equipped to purchase these metals. Because metals presented for sale may be from different areas and may be of varying composition, metal buying establishments must either smelt or assay such metals before they can, in turn, sell it to an establishment capable of processing it. As used herein, the term gold will be assumed to include other precious metals such as, but not limited to, silver, platinum, copper, etc.

Such gold or gold alloys may be located in areas not readily serviced by roads making the transportable, self-contained smelting and assay facility disclosed in U.S. patent application Ser. No. 13/364,422 filed Feb. 2, 2012 for Transportable Assay Facility and Method of Using Same to Procure and Assay Precious Metals, hereinafter the '422 application that is in turn a Continuation-in-Part application of U.S. patent application Ser. No. 13/136,811 filed Aug. 11, 2011 titled Transportable Assay Facility and Method of Using Same to Procure and Assay Precious Metals, hereinafter the '811 application unusable. However, as previously noted, both the '422 and '811 applications have been included herein by reference. Such transportable assay facilities are useless for providing smelting and assaying functions to locations that are not reachable by road. Therefore, the need exists for a transportable, self-contained assay facility for use in areas not served by roads. Such a transportable, self-contained assay facility may be delivered to a site by aircraft or other suitable means not dependent upon the existence of a road.

SUMMARY OF THE INVENTION

In accordance with the present invention there is provided a transportable, self-contained assay facility and a method of using the transportable, self-contained assay facility. Standardized shipping containers, also known as ISO containers are well known. Containerization is a system of freight transport based on a range of steel intermodal containers built to standardized dimensions. These containers can be loaded and unloaded, stacked, transported efficiently over long distances, and transferred from one mode of transport to another including container ships, rail and semi-trailer trucks, and aircraft.

A vast infrastructure for moving and handling such containers now exists internationally. While primarily used for transporting materials, this vast infrastructure may be utilized to transport a transportable, self-contained assay facility if one is built within one of such standard containers. This allows the placement of a transportable, self-contained assay facility virtually anywhere in the world.

A standard shipping container, typically an 8×8×20 foot size may be completely equipped to melt and assay precious metals, particularly gold and gold alloys. It will, of course, be recognized that other container sizes may be chosen to meet a specific need.

The container is typically portioned into three sections, a utility compartment, a processing compartment and a client compartment.

The utility compartment typically contains a three-phase, diesel powered electrical generator, an exhaust system having a HEPA filter, and a fuel supply tank.

The processing compartment contains an induction furnace designed to melt precious metals, a closed-loop chiller to cool the induction furnace, a quench tank, an accurate scale, typically an analytical balance to weigh precious metals, and X-ray fluorescence (XRF) alloy analyzer to provide an accurate assay of the content of an ingot.

The client compartment allows a client (i.e., a person with precious metal to be assayed) to be seated with a view through a window into the processing compartment such that he or she may observe every step of the assaying operation. This visibility for the client helps instill confidence in the client that the assaying operation is being performed honestly. In some cases, a closed circuit video monitoring system may also be included to allow a client clearly observe each step of the process taking place in the processing compartment.

In operation, client with precious metal to sell brings that precious metal precious metal to the transportable, self-contained assay facility where it is melted and poured into an ingot. After the ingot is cooled and dried, it is weighed and the exact weight is recorded in a computer. The ingot is then analyzed with the XRF analyzer and the XRF analysis of the ingot is then recorded in the computer.

A communications apparatus, typically a satellite phone or the like, within the transportable, self-contained assay facility is used to determine the current price of the precious metal of interest (usually gold) and that price is also entered into the computer. Using the data now in the computer, the value of one or more of the specific precious metal in the ingot is calculated.

The seller has several options. He or she may wish to receive the smelted ingot. In this case the seller pays the assayer a fee for the melting and assay and then leaves with the ingot. If the ingot is retained, it is placed in a safe and the seller may receive payment in the form of cash, a wire transfer, an open hedge, r physical bullion, or a check. Retained ingots are securely shipped to a processing facility. The exact mode of shipment depends on the location of the facility and the access to common carriers such as FedEx® or other such carriers offering secure shipping.

If the seller chooses to receive payment for the ingot as a wire transfer to his or her account, a wire transfer is initiated from within the transportable, self-contained assay facility.

Once a confirmation number is received from the issuing bank, the seller leaves the facility. The seller may be given an opportunity to communicate with his or her own bank to provide them the confirmation number.

If an open hedge (often known as leaving the precious metal in a pool) is chosen, the surrendered precious metals are processed and assayed so that the seller understands exactly how many ounces of metal that he/she has. The processor (e.g., Assay on Wheels®) then takes possession of the metal but does not immediately pay the seller. Rather, the seller then has the option to call the buyer/processor when the price of the surrendered metal reaches a certain price that's acceptable to the seller. The buyer/processor then hedges the metal into the market and pays the seller at that future time.

A client may, of course, be paid by cash or check.

It is, therefore, an object of the invention to provide a transportable, self-contained assay facility in a standard shipping container completely equipped to melt and assay scrap precious metal or metal rich ore.

It is another object of the invention to provide a transportable, self-contained assay facility where precious metal or precious metal ore may be melted using an induction or arc furnace powered by a self-contained generator and formed into ingots.

It is an additional object of the invention to provide a transportable, self-contained assay facility where ingots may be accurately assayed and wherein the current market price of gold or another precious metal may be determined so that a value may be immediately calculated for the ingot.

It is a further object of the invention to provide a transportable, self-contained assay facility where a computer calculates the worth of the seller's precious metal now in ingot form and where the seller may be paid for the precious metal in cash, gold bullion, by a wire transfer initiated and confirmed from the transportable, self-contained assay facility, by an open hedge, or by check.

It is a still further object of the invention to provide a transportable, self-contained assay facility security, surveillance, and communications system whereby the location, security, and other information concerning the transportable, self-contained assay facility may be monitored at a location remote thereto.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein:

FIG. 7 is a screen shot of a typical XRF analysis result;

FIG. 8b is a screen shot of a gold bar payout determination screen of a customer payout workbook;

DETAILED DESCRIPTION OF THE PREFERRED EMBODIMENT

The present invention provides a transportable, self-contained assay facility housed in a standard ISO "C" size shipping container and a method of using the transportable, self-contained facility.

Figure 1:
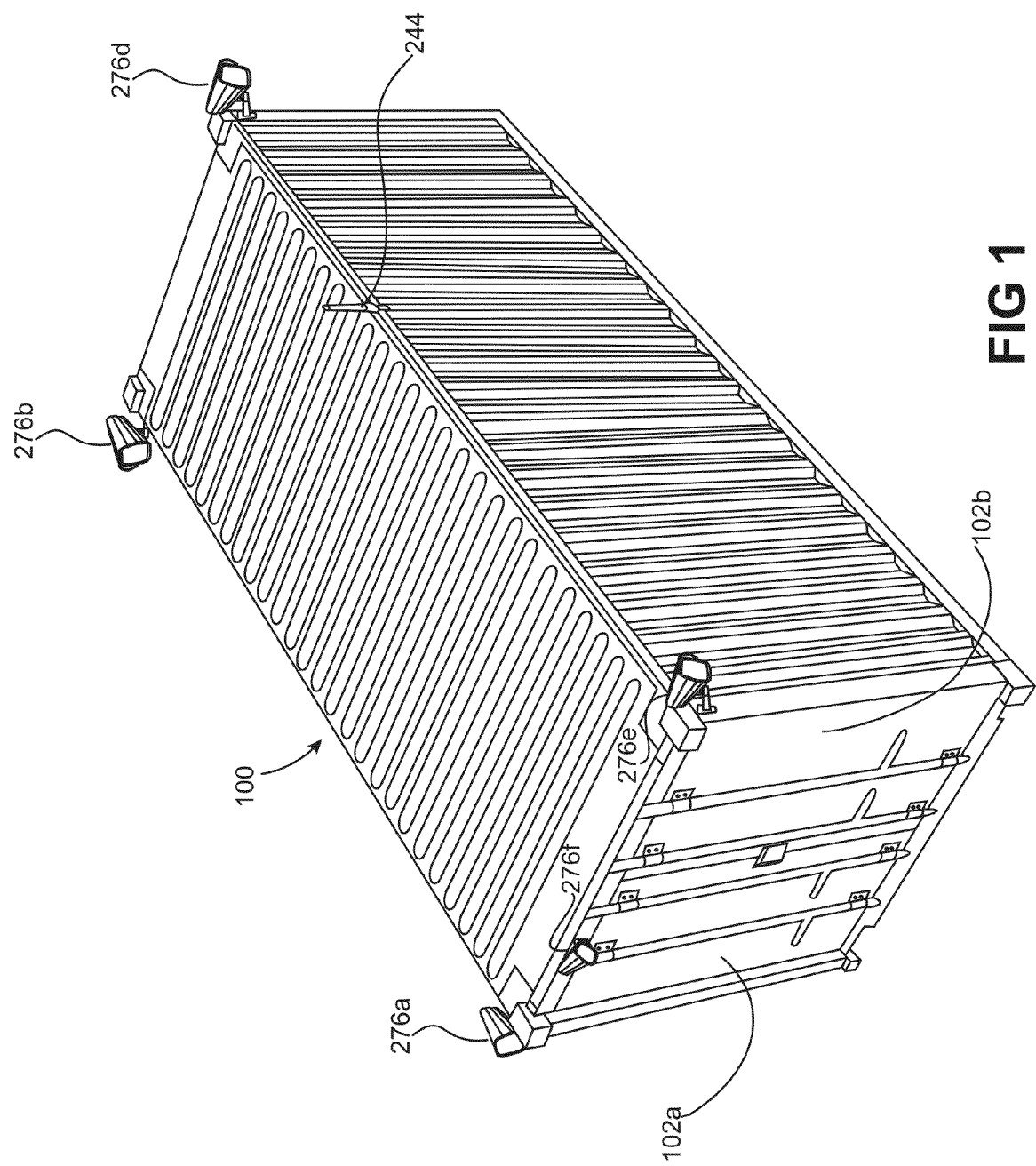
FIG. 1 is a perspective view of a standard ISO "C" size shipping container of the prior art before modification to house a transportable, self-contained assay facility.

Referring first to FIG. 1, there is shown perspective view of an 8×8×20 foot ISO "C" size container 100 with front doors 102a, 102b both closed prior to any modifications thereto. As used herein, the term front refers to the end of container 100 having doors 102a, 102b. As may readily be seen in FIGS. 2 and 3, doors 102a, 102b provide access to a client compartment 202. The term back refers to the opposite end of container 100 providing access to a utility compartment 204, best seen in FIGS. 2 and 5. While a "C" size container has been chosen for purposes of disclosure, it will be recognized that the novel transportable, self-contained assay facility could be built in standardized containers of other sizes. Consequently, the invention is not considered limited to an ISO "C" size container.

Figure 2:
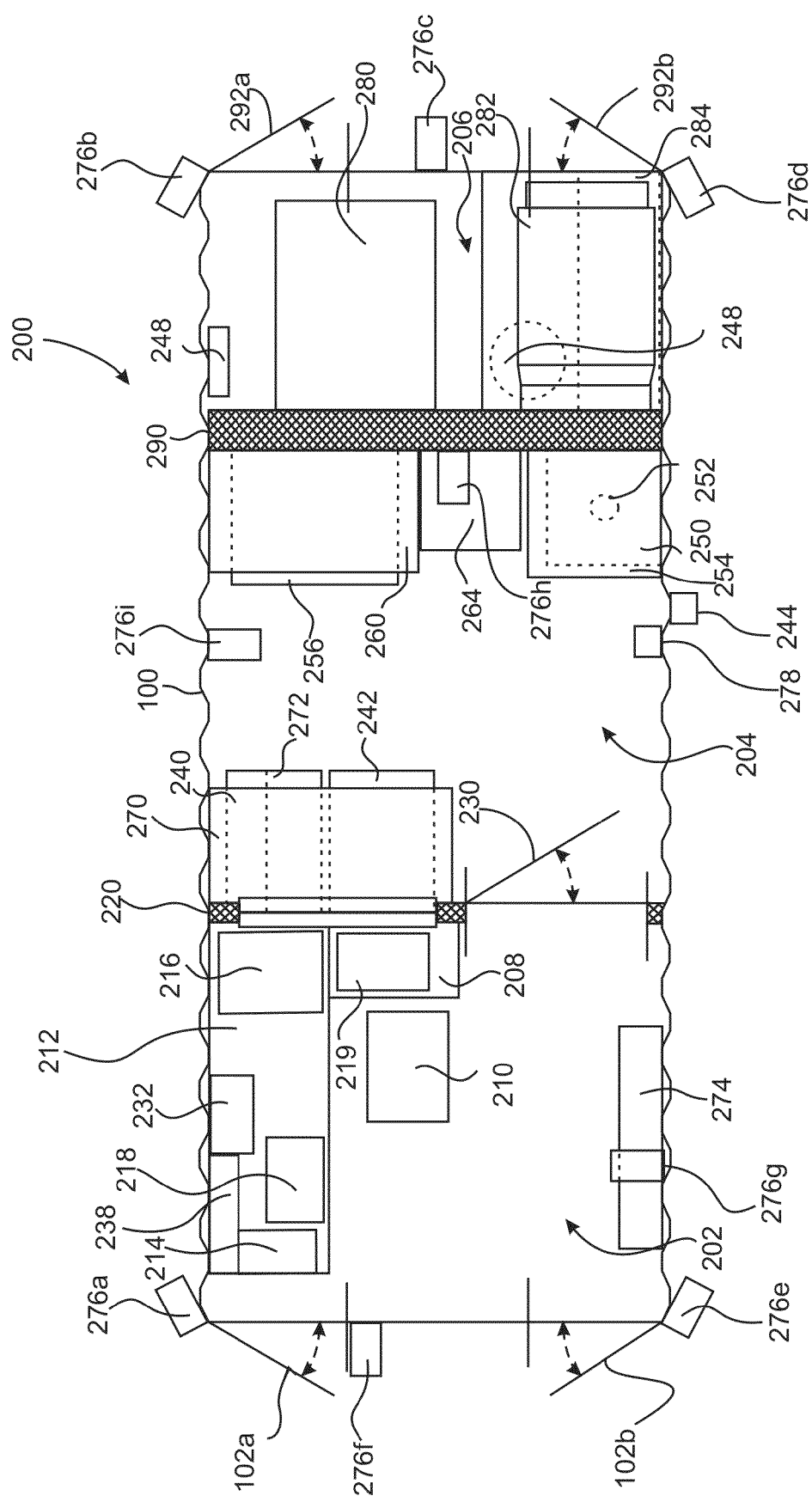
FIG. 2 is a simplified, schematic floor plan of the container of FIG. 1 after modification for use as a transportable, self-contained assay facility.
Figure 3:
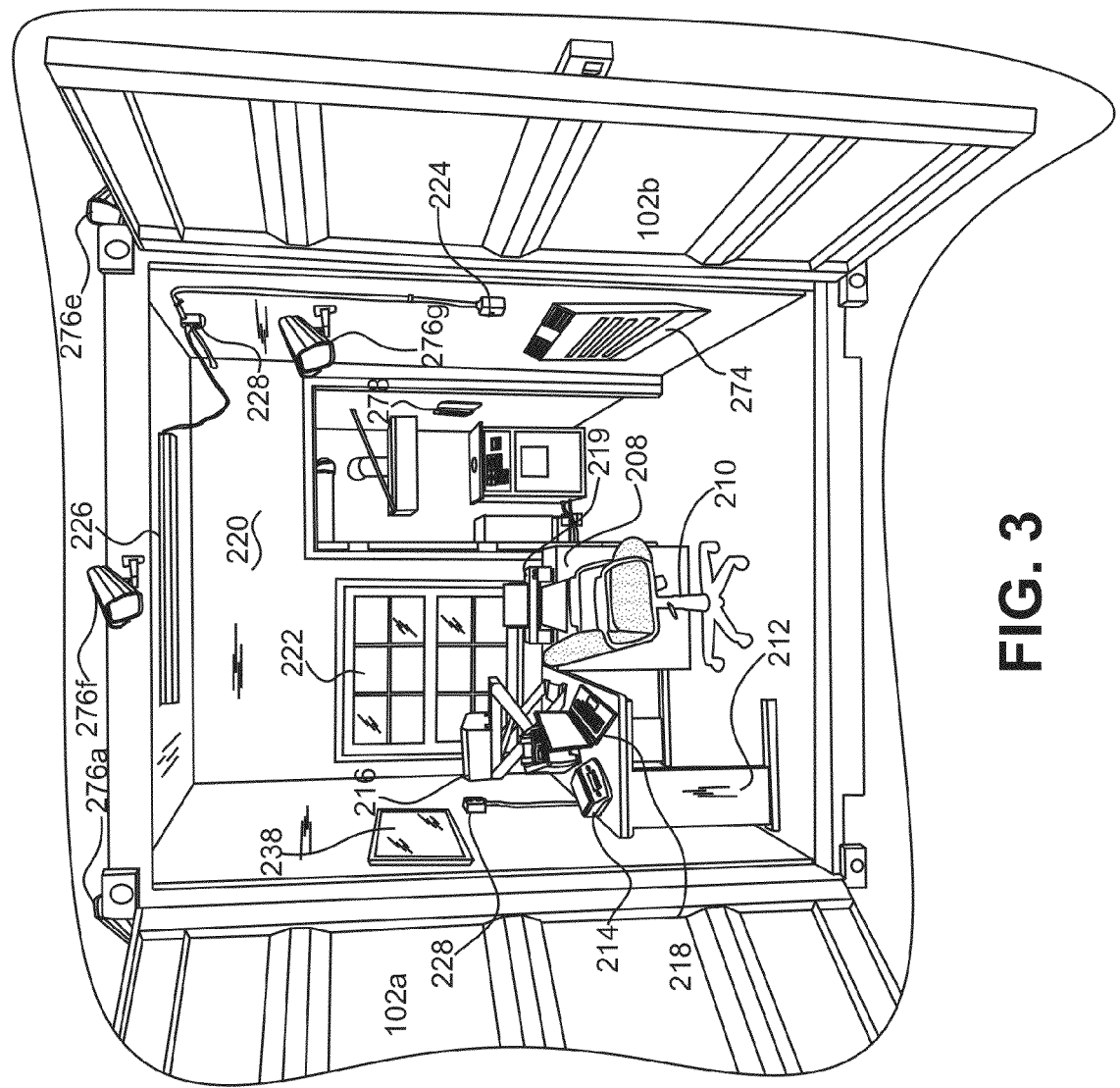
FIG. 3 is a front elevational, pictorial, schematic view of the transportable, self-contained assay facility of FIG. 2 showing the client compartment.

Assay facility 200 is divided into three major compartments, each described in more detail hereinbelow. Refer now also to FIGS. 2 and 3. FIG. 2 is a top plan schematic view of the container 100 of FIG. 1 modified for use as a transportable, self-contained assay facility 200. FIG. 3 is a front elevational, pictorial, schematic view of a client compartment 202 of transportable, self-contained assay facility 200.

A client compartment 202 is disposed at the front of facility 200 and is accessible from outside container 100 via doors 102a, 102b. Client compartment 204 typically contains a filing cabinet 208 having a printer 219 on an upper surface thereof and with a chair 210 adjacent thereto. An equipment stand 212 typically supports an accurate precision scale or balance, typically a so-called analytical balance 214, X-ray fluorescence (XRF) alloy analyzer 216, a cash counter 236, and a notebook computer or the like 218.

XRF analyzer 216 may be a Thermo Scientific Niton® Model XL3t XRF analyzer manufactured by Thermo Fisher Scientific of Billerica, Mass. This model has been found suitable for the application. Typically the Thermo Scientific Niton® Model XL3t analyzer 216 is mounted on a stand, not specifically identified, to facilitate use thereof. It will be recognized that other suitable XRF analyzers and/or similar analyzers using different analysis technologies may be substituted for the Thermo Scientific Niton® Model XL3t analyzer 216 chosen for purposes of disclosure. Consequently, the invention is not considered limited to a particular analysis device or technology as any suitable analysis apparatus may be utilized.

An accurate scale 214, typically an Analytical Balance such as an Ohaus Explorer® Pro analytical balance, Model EP6101N manufactured by Ohaus Corporation of Parsippany, N.J. has been found suitable for the application. As with other equipment used within assay facility 200, it will be recognized that other suitable scales or balances may be substituted for the Ohaus Model EP6101N and the invention is intended to include any suitable scale or balance.

A partition 220 separates client compartment 202 from processing compartment 204. A window 222 disposed in partition 220 allows viewing all activities in processing compartment 204 from client compartment 202.

Processing facility 200 has self-contained electrical power provided by a generator 280 disposed in utility compartment 206. Electrical service exemplified by light switch 224, overhead light 226, and electrical outlet 228 are all connected to generator 280.

A door 230 allows passage between client compartment 202 and processing compartment 204.

Figure 4:
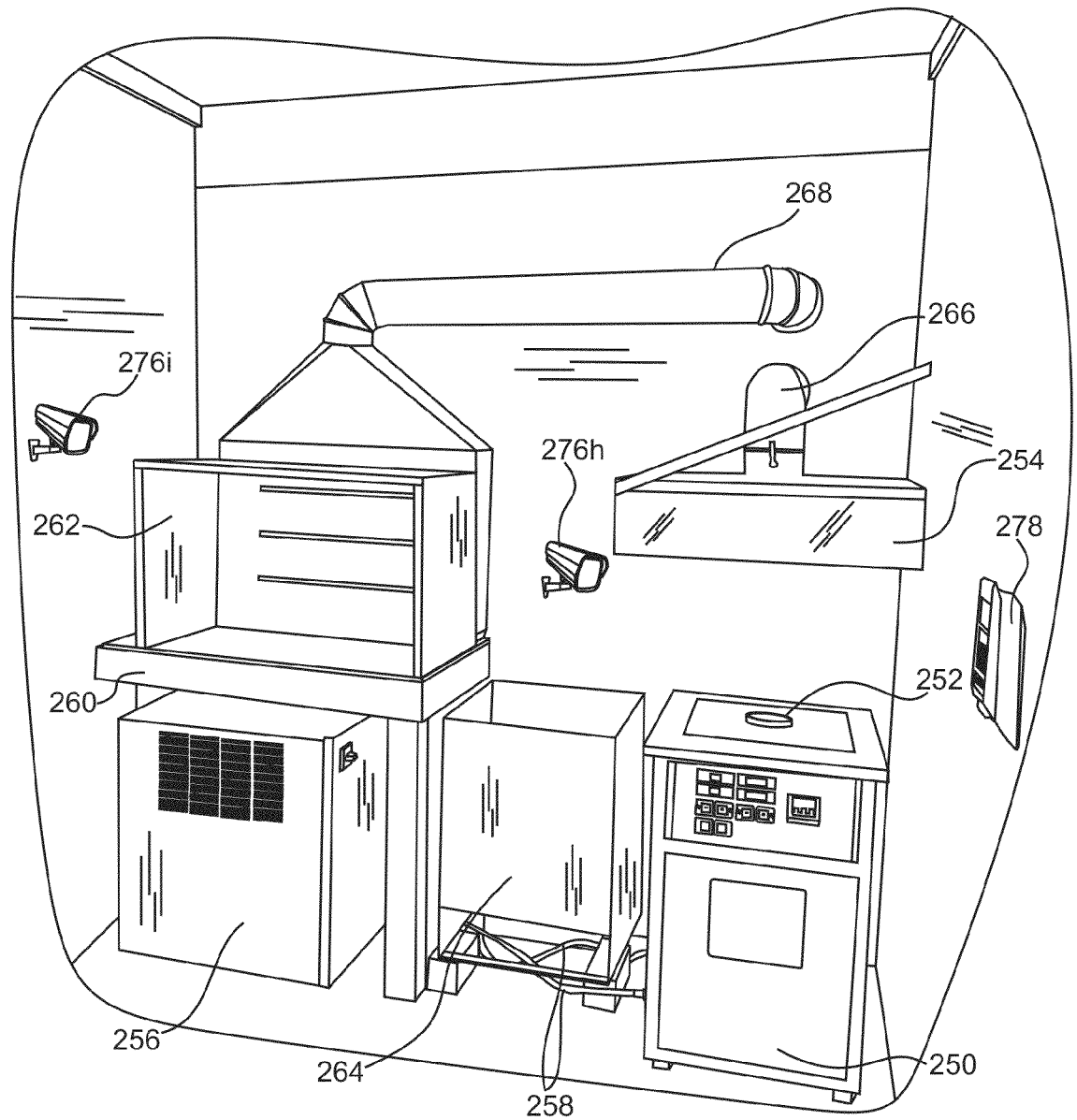
FIG. 4 is a front elevational, pictorial, schematic view of the transportable, self-contained assay facility of FIG. 2 showing the processing compartment.

Referring now also to FIG. 4, there is shown a front, elevational, pictorial, schematic view of processing compartment 204. Processing compartment 204 contains the necessary equipment to extract desired precious metal (e.g., gold) from scrap jewelry, ore, etc. Gold processing compartment 204 may be viewed from client compartment 202 through window 222 or by means of a closed circuit video monitor 238 discussed in more detail hereinbelow.

Processing compartment 204 contains an induction furnace 250 having an opening 252 to receive a crucible, not shown, for melting the precious metal. An induction furnace exhaust hood 254 is disposed over induction furnace 250. A CEIA Model F5-D/220 induction furnace manufactured by CEIA SpA of Arezzo, Italy has been found suitable for the application. It will be recognized that other similar induction or arc furnaces may be known to those of skill in the art, any suitable one of which may be substituted for the CEIA furnace chosen for purposes of disclosure.

A chiller 256 is operatively connected to induction furnace 250 and provides necessary cooling water to induction furnace 250 via conduits 258. A Dimplex Thermal Solutions Chiller Model No. JH1000-21-V has been found suitable for the application. The JH1000-21-V chiller is a closed-loop device that incorporates a high pressure recirculating pump with a capacity of 4 gpm at 50 psi and has a ⅛ ton capacity. It will be recognized that other chillers made by other manufactures may be suitable for the application. Consequently, the invention is intended to include any suitable chiller in addition to the Dimplex JH1000-21-V chiller chosen for purposes of disclosure.

A workbench 260 is disposed over chiller 256 and has a workbench exhaust hood 262 over its upper surface.

An ingot quench tank 264 is disposed between workbench 260 and induction furnace 250.

Both induction furnace exhaust hood 254 and workbench exhaust hood 262 are coupled by exhaust ducts 266, 268, respectively to an approximately 3500 cfm belt-driven exhaust blower 282 (best seen in FIG. 5) located in utility compartment 206.

A work table 270 is also disposed in processing compartment 204.

Also located in processing compartment 204 is a safe 272, typically placed under work table 270. Any type of safe that has the capacity to store precious metal received from a seller and cash from which to pay a seller may be used for the application. In some environments, a removable safe 272 may be preferred so that safe 272 may be removed when assay facility 200 is not in use. In still other environments, safe 272 may contain a built-in cash dispenser 240. Cash dispenser 240 is accessible from the front of safe 272 such that safe 272 need not be opened to dispense cash.

A storage cabinet 242 may be placed adjacent safe 272 under table 270.

An air conditioner 274 allows transportable, self-contained assay facility 200 to operate in hot locations. Typically, air conditioner 274 is a combination air conditioner and heater that allows operation under either hot or cold conditions. In some embodiments, air conditioner 274 is portable and may readily be moved between customer compartment 202 and processing compartment 204 as desired.

One or more inside and outside security cameras 276a . . . 276i may be used to monitor all activity within and outside transportable, self-contained assay facility 200. Images from security cameras(s) 176a . . . 176i may be recorded and stored locally or may be periodically uploaded via a satellite phone communications system 278. Images may be recorded and stored on notebook computer 218 using "DVR" software well known to those of skill in the art. Notebook computer 218 also contains other security system elements and controls.

A variety of security alarm inputs including but not limited to motion sensors, pressure sensors, vibration sensors, glass breakage sensors, safe intrusion sensors, sound sensors, fire sensors, power failure sensors, panic buttons, or any other known sensor or input, none of which are specifically identified may be connected to notebook computer 218. When an alarm condition is sensed, the assayer is alerted using Satellite phone communications system 278. The security system forms a so-called silent alarm where no local audible or visual annunciators are provided or used. However, it will be recognized that such local annunciators may be provided and used when required in specific installations.

Satellite phone communications system 278 typically utilizes a satellite phone amplifier and external antenna disposed outside container 100.

A remote monitoring system may be installed with one or more cameras, 276h, 276i in processing compartment 204 and a video monitor 238 disposed in client compartment 202. Such a remote monitoring system allows a client in the client in client compartment 202 to better monitor the activities in processing compartment 204. Such monitoring systems are believed to be well known to those of skill in the security arts and, consequently, such systems are not further described or discussed herein.

Further, video monitor 238 may serve as part of a security system by allowing viewing selected ones of security cameras 276a . . . 276f. Security cameras 276a . . . 276f are typically viewed on notebook computer 218 and video monitor 238 may also be connected thereto.

Figure 5:
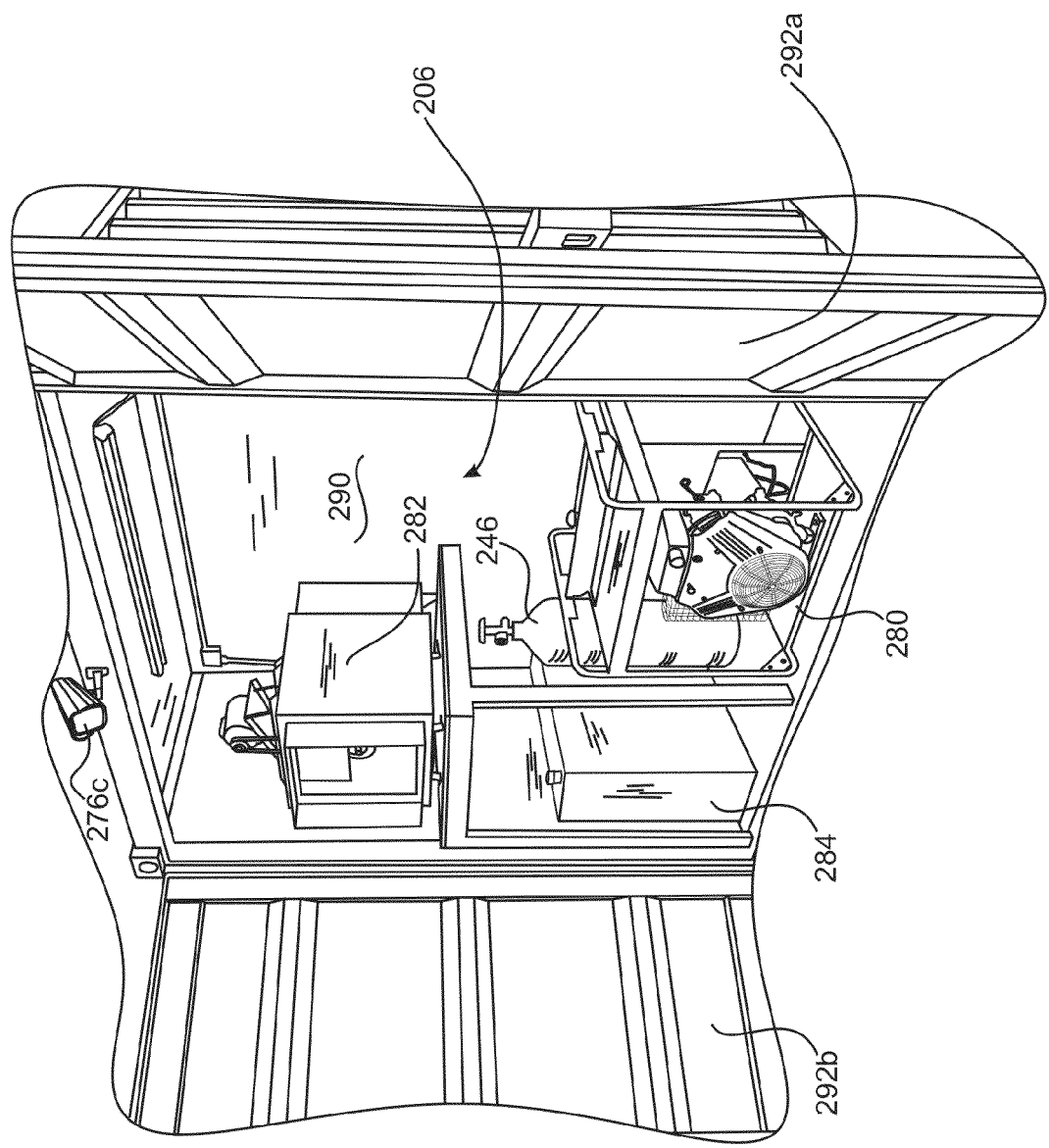
FIG. 5 is a rear elevational, pictorial, schematic view of the transportable, self-contained assay facility of FIG. 2 showing the utility compartment.

Referring now also to FIG. 5, there is shown a rear elevational, pictorial, schematic view of utility compartment 206 as viewed from the back of container 100.

Two major system components are housed in utility compartment 206. First, a three-phase, diesel-powered generator 280 provides approximately 12 kW of electrical power to assay facility 200. While a Kubota Model 10012ENC, Engine type V1505BG has been chosen for purposes of disclosure, it will be recognized that other similar generators available from other manufacturers may be substituted. Consequently, the invention is not considered limited to a particular make or model of generator. Rather, the invention is intended to include any suitable generator. Assay facility 200 is designed and adapted for deployment anywhere in the world. Because all power is derived from generator 280, there is no need to rely on or accommodate power of different voltage (e.g., 117, 208, 220/230, 440, etc.), or frequencies (e.g., 25, 50, 60, or even 400 Hz) available in different parts of the world. Because assay facility 200 is designed for use in remote locations, power, even when available, may not be reliable or available in enough quantity to operate the induction furnace 250 and other apparatus in assay facility 200.

An external fuel supply tank 284 is used to provide fuel for generator 280.

The second major component in utility compartment 206 is exhaust system 282. Exhaust system 282 includes an approximately 3500 cfm blower system to draw fumes from induction furnace exhaust hood 254 and workbench exhaust hood 262 through exhaust ducts 266, 268, respectively. The exhaust system is sized to allow a complete air replacement in the client compartment 202 and processing compartment 204 approximately every 17.5 seconds and typically contains a HEPA filter, not specifically identified. The HEPA filter removes most of the particles from the air being exhausted from inside truck assay facility 200, typically approximately 99.9% of particles greater than 0.3 microns.

Because generator 280 and exhaust blower 282 may generate large amounts of acoustical noise, utility compartment 206 is isolated from processing compartment 204 by a thick, sound isolating partition 290. In the embodiment of assay facility 200 chosen for purposes of disclosure, sound isolating partition 290 is approximately 8-12 inches thick. Sound isolating partition 290 is constructed using well-known sound isolating construction practices and materials, for example Levelrock™ Sound Reduction Board manufactured by United States Gypsum Company (USG) of Chicago, Ill., or other similar materials. Consequently, the invention is not considered limited to a particular sound isolating construction technique or material or materials.

Other items possibly housed in utility compartment 206 might be a water tank, shelves or cabinets, housing for electronic communication and/or security equipment, none of which are specifically identified.

A provision is included in the aforementioned plumbing to introduce compressed air to purge all lines when necessary so that damage due to freezing is eliminated. A compressed air tank 246 in utility compartment 206 supplies compressed air for this purge.

In operation, the transportable, self-contained assay facility 200 is delivered to a desired location, typically by an aircraft, either fixed wing or rotary wing) and placed in a level location. Once in place, container 100 is opened and all equipment is unpacked and installed. All external features such as security cameras 276a . . . 276f, satellite phone amplifier and external antenna 244, and air conditioner 274, etc. are installed.

Diesel fuel is added to storage tank 284.

Once generator 280 is started, operation of transportable, self-contained assay facility 200 may begin.

Figure 6A:
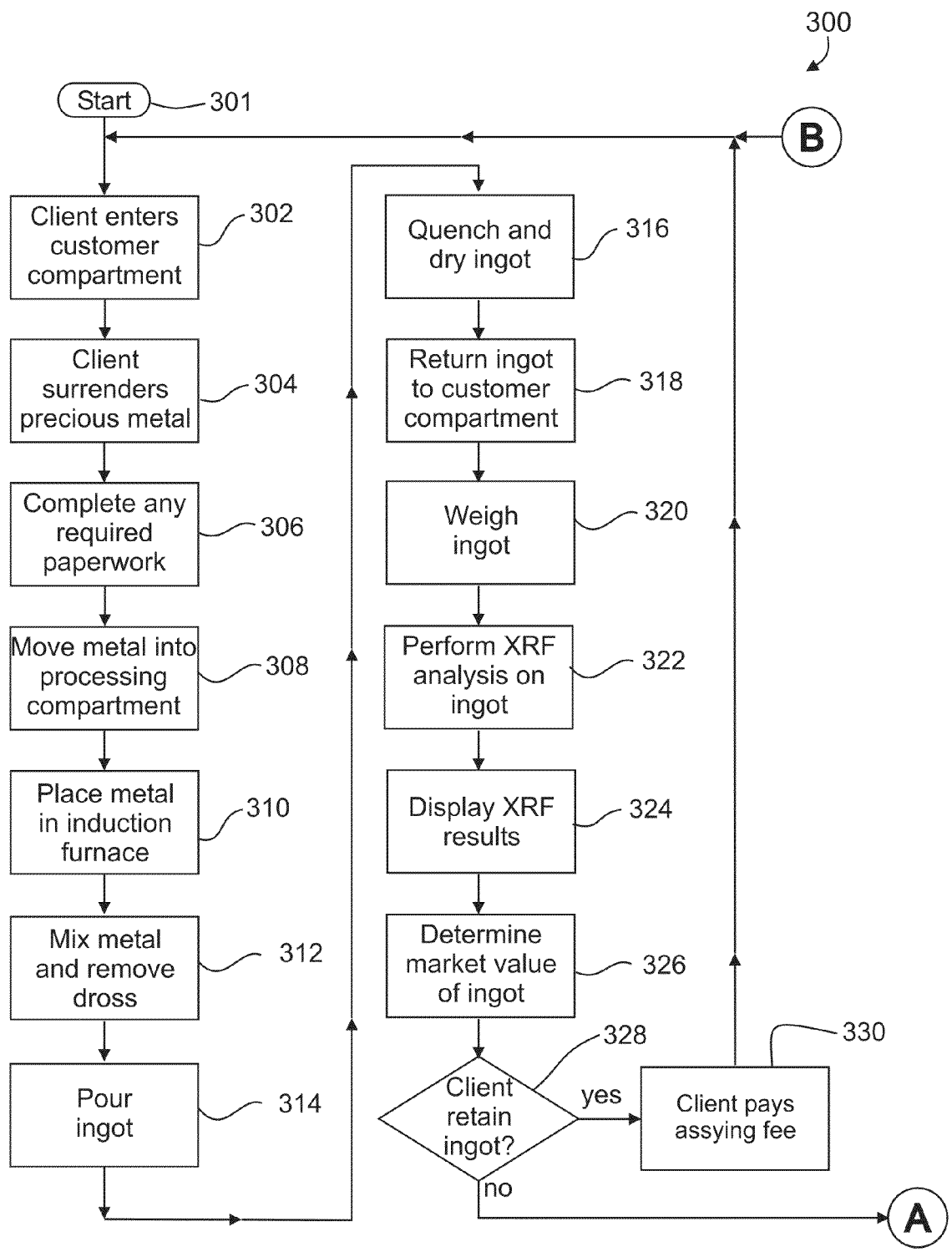
FIGS. 6a and 6b when taken together form a simplified flowchart of the operation of the transportable, self-contained assay facility in accordance with the invention.
Figure 6B:
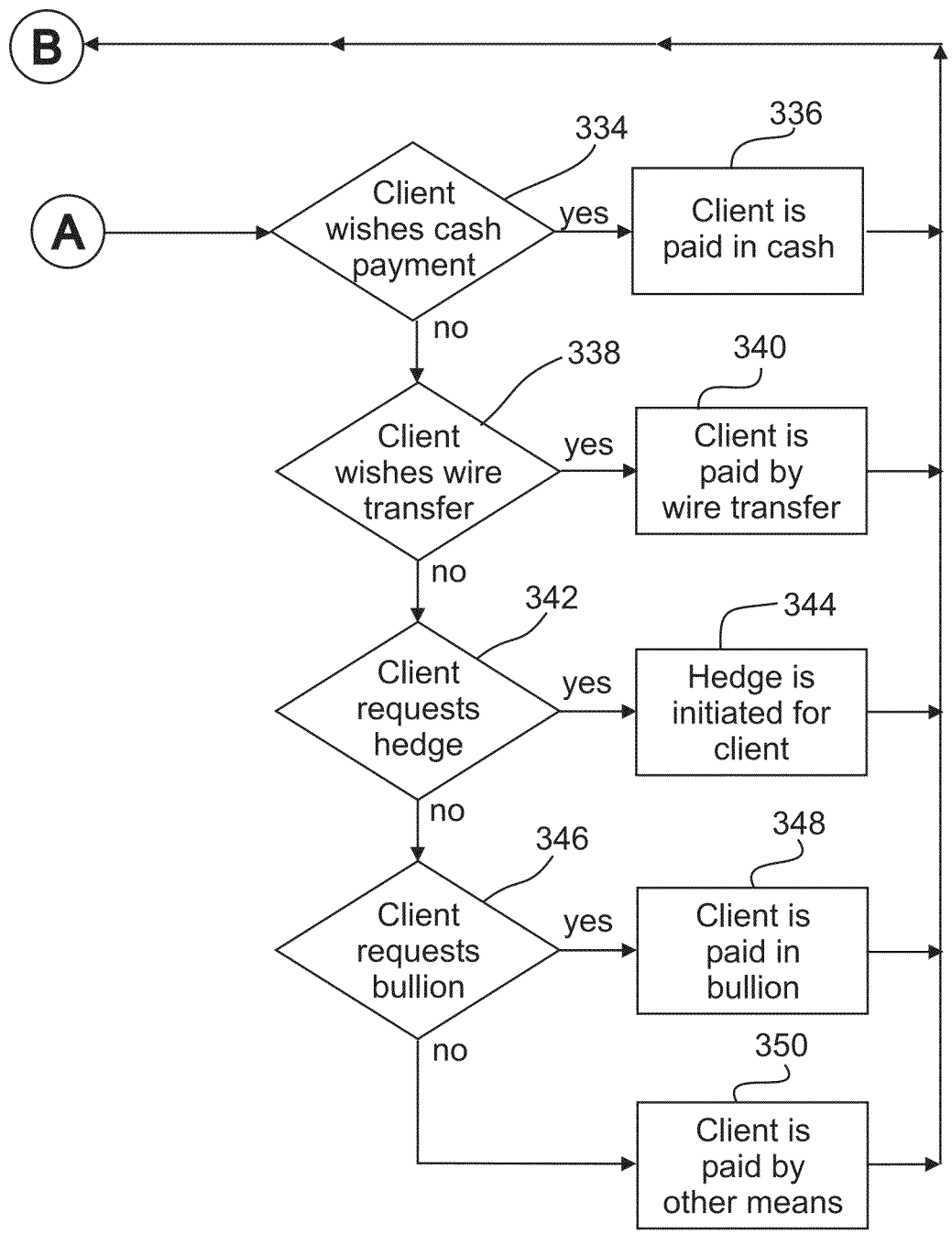

Referring now to FIGS. 6a and 6b there is collectively shown a flow chart of the transportable, self-contained assay process of the invention, generally at reference number 300.

A client wishing to have precious metal smelted and assayed brings such precious metal or metal rich ore to the facility where the client enters the client compartment 202, block 302 and surrenders his/her precious metal to an assay technician, block 304.

When required any necessary paper work for compliance with 13 C.F.R. §103.140 or other anti money laundering statutes must be completed, block 306.

The surrendered precious metal is weighed using precision scale 214, step not shown.

The assay technician moves the surrendered precious metal into processing compartment, block 308 and places material to be melted/smelted into a crucible that is then placed into induction furnace 250, block 310 while client watches from client compartment 202 through window 222, block 310. It is assumed that induction furnace 250 has been started and allowed to reach a desired melting temperature, generally approximately 2000° F. Precious metal is generally added to the crucible in small amounts. The melted precious metal mix is periodically stirred to obtain a uniform mixture of the component metals of the batch. Unmelted metals such as Platinum (Pt) are removed from the melt as is dross, block 312.

When the melt is at an appropriate temperature, considered to be uniform, and is free from dross, the crucible is removed from induction furnace 250 and the contents are poured into an ingot mold of an appropriate size, block 314.

Once the poured ingot has cooled sufficiently for safe handling, the ingot is removed from the ingot mold and placed into ingot quench tank 264 for rapid cooling, block 316.

When cool, the ingot is removed from ingot quench tank 264. The ingot is then dried, block 316. Once dried, the assay technician returns the ingot to client compartment, block 318.

The ingot is then weighed using precision scale 214. After weighing, block 320, the ingot is scanned by XRF analyzer 216, block 322 and the results of the X-ray analysis recorded and displayed, block 324. A screen shot of a typical analysis result is shown in FIG. 7. As may readily be seen, the percentage and a two sigma value for various component metals of the ingot are displayed. In the example shown in FIG. 7, gold (Au) forms 59.66 with a 2σ value of 0.88. Likewise, the percentage of Silver (Ag), Palladium (Pd), Platinum (Pt), Zinc (Zn) and copper (Cu) are displayed.

The current market value of the ingot is next determined, block 326. The market value of ingot depends on the market value of one or more selected component precious metals (e.g., gold, silver, etc.). The value of the selected precious metal(s) (e.g., gold, silver, etc.) is calculated by multiplying the current market value of each selected metal by the percentage of that metal (obtained by the XRF analysis) in the ingot multiplied by the total weight of the ingot. Weights are typically expressed in ounces although it will be recognized that other units of measure, for example, grams may be used for such calculations. The current market value of the selected precious metal(s) is determined typically using computer 218 connected to a metal exchange or wholesale metal broker using the facility's communications system.

Once the market value of the precious metal is known, a client payout for the ingot may be calculated.

Figure 8A:
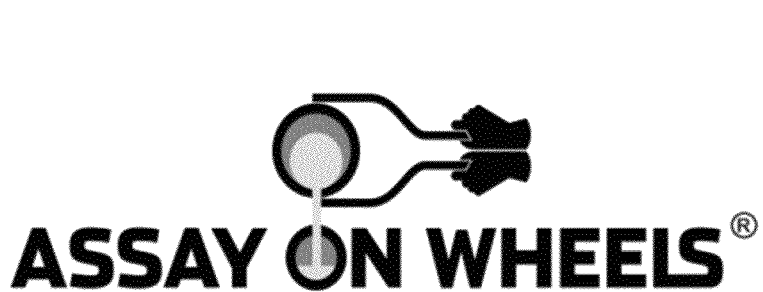
FIG. 8a is screen shot of a "welcome" screen of a "customer payout workbook" used to determine the payout to a client in accordance with the method of the invention.
Figure 8A:
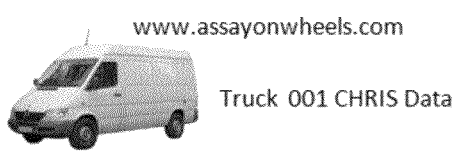
Figure 8A:
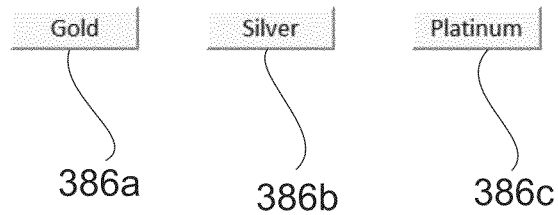

Customer payout is calculated using a series of spread sheets or other similar programs, not shown, forming a "customer workbook" in computer 219. Referring now also to FIG. 8a, there is shown a welcome screen 380 that allows the assay technician, not shown, to enter preliminary identification information. This information includes a customer identification 382 and a processor (i.e., assay technician) 384.

Once the preliminary information is entered, the "Save" button is selected and the template is saved as a unique file name before choosing metal type. The assay technician then selects the particular precious metal with which to begin, buttons 386a, 386b, 386c. In the implementation chosen for purposes of disclosure, gold (button 386a), silver (button 386b), and platinum (button 386c) are shown. It will be recognized that one or more of precious metals gold, silver, and platinum may be removed. Other precious metals may be added. Consequently, the invention is not considered limited to the particular precious metals chosen for purposes of disclosure. The invention is intended to include any combination of precious metals.

Figure 8C:
FIG. 8c is a screen shout of gold bar hedge payout screen of a customer payout workbook.
Figure 8D:
FIG. 8d is a screen shot of a "Totals" screen of a customer payout workbook.

A variety of different screen, (e.g., spreadsheets, etc) are provided to calculate customer payout for various precious metals or combinations thereof, different payout options, and for multiple assayed bars. Only three of such payout screens are shown. Referring now also to FIG. 8b, there is shown a payout calculation screen 390 for a single gold bar. FIG. 8c shows a payout calculation screen 420 for establishing an open hedge for one or more gold bars. FIG. 8d shows a totals screen 450 for determining a total customer payout for multiple bars and/or multiple precious metals. They are chosen as representative of any number of possible of payout screens in a customer payout workbook. It will be recognized to those of skill in the art that numerous other payout screen may be provided to meet particular operating circumstances or environments. Consequently, the invention is not considered limited to the customer payout screens 380, 390, 420, and 450 chosen for purposes of disclosure. Rather, the invention is intended to include any and all additional customer payout screens useful for use in assay facility in accordance with the method of the invention.

As shown in FIG. 8b, the assay technician is next provided with a customer payout screen 390 because the selected precious metal is gold and button 386a (FIG. 8a) was selected. Other similar screens, not shown, could be provided for silver (button 386b) or platinum (button 386c).

On customer payout sheet 390 as series of X-ray results, not specifically identified, are shown. Values for these X-ray fields are automatically provided to computer 219 by XRF analyzer 216 when the particular gold bar was assayed.

The percent (%) purity value resulting from the X-ray analysis, block 322 has also been transferred to customer payout sheet 390 and shown at reference number 392. The total ounces of gold 396 is calculated by converting (when necessary) the bar or ingot weight in grams 394 to ounces and multiplying by the % pure, 392. These calculations are typically performed by computer 219.

The market price of gold obtained at block 326 is also transferred to form customer payout form 390 at reference number 398.

A total amount 400 is obtained by multiplying the total ounces of gold 396 by the current market price 398.

A payout percentage 402 is selected from a pull-down menu and a total payout 404 is calculated from total amount 400 multiplied by payout percentage 402.

A processing 406 fee selected from another pull-down menu and subtracted from payout total 404 Processing fee 406 is subtracted from the payout total 404.

Shipping cost, if any, 408 is also subtracted from payout total 404.

After subtraction of processing fee 406 and shipping fee 408 from payout total 404, the net customer payout 410 remains.

There are several ways in which the client may be paid for the ingot. One way is to simply return the ingot to the client. If the client wishes to retain the assayed ingot, block 328, the client may be charged a processing fee for the assays, block 330. Once the processing fee is collected, either in cash, credit card, or by another arrangement, block 330, the ingot is returned to the client. A client payout form 380 (FIG. 8) may be printed and given to the client. The client then typically leaves and control is transferred to block 301.

If the client wishes to surrender the ingot, block 328, the payment form is agreed upon. If the client requests cash, block 334, the assay technician collects the necessary cash payment from cash dispenser 240 housed in safe 272, typically disposed in processing compartment 204, and places the ingot in the safe 272, block 336. Once the client is paid, he or she typically leaves and control is returned to start, block 301.

If however, the client does not want a cash payment, block 334, the client may request a wire transfer, block 338. If the client wishes to be paid by wire transfer, block 338, a wire transfer is initiated, block 340. Typically, a client does not leave assay facility 200 until a verification of the wire transfer, including a confirmation number, is received and provided to the client. Once the client is satisfied that the wire transfer has been successfully initiated, block 340, he or she typically leaves and control is returned to block 301. The retained ingot is typically placed in the safe 272.

If the client wishes neither a cash payment nor a wire transfer, he or she may opt that a market hedge be established, block 342. If the client requests a hedge, a hedge is initiated for the client, block 344. Referring now also to FIG. 8c, there is shown a client payout screen 420 showing the initiation of a hedge. Up to three gold bars 422, 424, 426 may be processed. Once the client has read the acknowledgement paragraph, the processor signs the form 428. The client then provides a printed name 430 and a signature 432. If a Patriot Act signature is required, that signature 434 is also supplied. Once the hedge is initiated, the client typically leaves and control is transferred to block 301. The retained ingot is typically placed in the safe 272.

If, however, the client does not opt for a hedge, block 342, the client may wish to be paid in bullion, block 346. If the client requests a payment in bullion, block 346, the assay technician removes the required amount of bullion from the safe 272, block 348, and pays the client. Once the client is paid, he or she typically leaves and control is returned to block 301. The retained ingot is typically placed in the safe 272.

If the client has not opted for payment in cash, block 334, wire transfer, block 338, a market hedge, block 342, or bullion, block 346, the client may be paid by check or in some other mutually acceptable manner, block 350. The retained ingot is typically placed in the safe 272. The client typically then leaves and control is transferred to block 301.

Referring now also to FIG. 8d, there is shown a client payout totals screen 450. Totals screen 450 is useful for complex transactions relating to multiple precious metals and especially multiple ingots (i.e., bars), or split (i.e., payment paid in more than one manner) payout methods are to be made.

Information from other customer payout screen may be summarized on totals screen 450. Multiple bars 460, each potentially having more than one precious metal are enumerate in columns 452 (gold), 454 (silver), and 456 (platinum) with the dollar total dollar amount associated with each bar tallied on respective lines in column 458.

If there is a wire transfer fee 462 associate with the client transaction, the fee is subtracted from the sum of dollars column 458 and the total less the wire transfer fee is shown as total payment 464.

As previously described, the processor signature 428, the client's printed name 430, the clients signature 432, and, when required, a Patriot Act compliant signature 434 are gathered on the form resulting from customer payout totals screen 450.

If the client has surrendered the ingot, it will typically be put into safe 272. Periodically, for example, at the end of a day, the accumulated ingots may be picked up by a bonded courier for shipping.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A transportable, self-contained assay facility, comprising:
   a) a closed, sealable, shippable container suitable for containing all tools and equipment required to melt/smelt and assay precious metals, said container being adapted to allow a seller of precious metals to observe the melting and assaying processes;
   b) a scale disposed within said container and positioned within view of said seller, said scale being adapted to output a signal representative of a weight of an object weighed thereupon;
   c) a furnace disposed in said container adapted to melt/smelt precious metal received from said seller, said furnace disposed within view of said seller and adapted to melt said precious metal to produce an ingot;
   d) an X-ray fluorescence (XRF) alloy analyzer disposed in said vehicle within view of said seller and adapted to analyze said melted ingot and to record and display the results of an analysis thereof;
   e) means for determining a current market price of at least one precious metal present in said ingot, said means for determining being disposed proximate said container;
   f) a computer disposed within said container and adapted to receive at least said signal representative of a weight of an object weighed received from said scale, an output recorded by said XRF analyzer, said determined current market price of said particular precious metal of interest and adapted to perform at least a calculation of the market value of said precious metal component of said ingot; and
   g) a printer disposed within said container and operatively connected to said computer and adapted to print at least the result of said calculation.

2. The transportable, self-contained assay facility as recited in claim 1, wherein said container comprises at least three compartments separated one from another therewithin.

3. The transportable, self-contained assay facility as recited in claim 2, wherein said at least three compartments comprise: a client compartment, a processing compartment, and a utility compartment.

4. The transportable, self-contained assay facility as recited in claim 3, wherein said furnace comprises:
   i) an induction furnace disposed in said processing compartment;
   ii) a tank of coolant operatively connected thereto;
   iii) a chiller disposed in said utility compartment and operatively connected to said induction furnace and said tank of coolant; and
   iii) an exhaust hood disposed adjacent said induction furnace and adapted to remove fumes generated by said induction furnace from within said processing compartment.

5. The transportable, self-contained assay facility as recited in claim 3, further comprising:
   h) an ingot quenching tank disposed proximate said induction furnace within said processing compartment of said container.

6. The transportable, self-contained assay facility as recited in claim 3, further comprising:
   h) a safe disposed within said container and adapted to receive at least said ingot.

7. The transportable, self-contained assay facility as recited in claim 3, wherein said computer is of a type selected from the group: laptop computer, notebook computer, netbook computer, tablet computer, and other portable computer system.

8. The transportable, self-contained assay facility as recited in claim 3, further comprising:
   h) an electrical generator disposed in said utility compartment and configured to supply electrical power to at least said furnace.

9. The transportable, self-contained assay facility as recited in claim 8, wherein said electrical generator comprises a three-phase, diesel powered electrical generator.

10. The transportable, self-contained assay facility as recited in claim 3, further comprising:
    h) an air compressor disposed in said utility compartment.

11. The transportable, self-contained assay facility as recited in claim 3, further comprising:
    h) an air conditioner disposed in one selected from the group: said client compartment and said processing compartment.

12. The transportable, self-contained assay facility as recited in claim 3, further comprising:
    g) a sound isolating partition disposed between said processing compartment and said utility compartment.

13. The transportable, self-contained assay facility as recited in claim 2, wherein said container is a modified ISO standard shipping container.

14. The transportable, self-contained assay facility as recited in claim 13, wherein said container is selectively convertible between a shipping configuration and an operational configuration.

15. The transportable, self-contained assay facility as recited in claim 14, wherein when said container is in said shipping configuration, an external surface of said container is free of any external feature that could interfere with shipping said container within a standard containerized freight shipping system.

16. The transportable, self-contained assay facility as recited in claim 2, further comprising:
    h) communications system disposed in said container for establishing and maintaining at least digital communication with a location remote from said container and for providing Internet access to said transportable, self-contained assay facility.

17. The transportable, self-contained assay facility as recited in claim 13, wherein said container has a length selected from the group: 20 feet, 30 feet, and 40 feet.

18. The transportable, self-contained assay facility as recited in claim 1, further comprising:
    h) a security and surveillance system disposed in and around said container, said security and surveillance system comprising:
       i) at least one camera disposed at a location selected from the group: inside said client compartment, inside said processing compartment, and outside said container;
       ii) a monitor disposed inside said container operatively connected to display an image from said at least one camera;
       iii) a digital video recorder operatively connected to and adapted to record an image from said at least one camera;
       iv) a communications link operatively connected to at least one of said at least one camera and said digital video camera operatively connected to each thereof and adapted to transmit at least an image therefrom to a receiver at a location remote from said container.

19. The transportable, self-contained assay facility as recited in claim 18, wherein said security and surveillance system further comprises:
- v) at least one alarm input selected from the group: motion sensors, pressure sensors, vibration sensors, glass breakage sensors, safe intrusion sensors, sound sensors, fire sensors, power failure sensors, panic buttons, other alarm sensors; and
- vi) at least one local annunciator selected from the group: bells, sirens, lights, or annunciators devices.

* * * * *